United States Patent [19]

Fromageot et al.

[11] Patent Number: 5,356,794
[45] Date of Patent: Oct. 18, 1994

[54] PURIFIED ENZYMATIC PREPARATION DERIVED FROM *CHROMOBACTERIUM VIOLACEUM*, METHOD FOR PREPARING IT AND ITS USE IN THE PRODUCTION OF α,β-DEHYDROTRYPTOPHANYL-PEPTIDES

[75] Inventors: Pierre Fromageot, le Chesnay; Roger Genet, Limours, both of France

[73] Assignee: Commissariat a l'Energie Atomique, Paris, France

[21] Appl. No.: 941,218

[22] Filed: Sep. 4, 1992

[30] Foreign Application Priority Data

Sep. 5, 1991 [FR] France .................................. 91 10973

[51] Int. Cl.$^5$ .................. C12P 21/00; C12N 9/04; C12N 9/06; C12N 9/08
[52] U.S. Cl. .................. 435/68.1; 435/190; 435/191; 435/192
[58] Field of Search ............... 435/190, 191, 192, 68.1

[56] References Cited

PUBLICATIONS

Takai (1980) *Dev. Biochem.*, 16, 103–115.
Kanda et al. (1990) "Amino Acids; Chem. Biol. Med., [Pap. Int. Cong. Amino Acids Res.]", Meeting Date 1989, pp. 1052–1058.
Ed., Lubec et al., ESCOM, Leiden, Neth.
Takai et al. (1987) *Meth. Enzymol.*, 142, 195–217.
Gustafson et al. (1977) *J. Chem. Soc. Chem. Comm.*, 23, 842–843.
Takai et al. (1977) *J. Biol. Chem.*, 252(8), 2648–2656.
Roberts et al. (1977) *J. Biol. Chem.*, 252(8), 2640–2647.
Cardillo et al. (1975) *J. Chem. Soc. Chem. Comm.*, 778–779.
Davis et al. (1976) *J. Bacteriol.*, 126(1), 544–546.
Narumiya (1979) *J. Biol. Chem.*, 254(15), 7007–7015.
Akira et al. (1991) *Chem. Abst.*, 115(17), 405, Abst #177920.
A. Maelicke, et al., "An Enzymatic approach to the labeling of tryptophan residues in peptides and proteins", Jan. 1978, pp. 296–300.
Pinto-Alphandary, et al., "Asymmetric titration of N-acetyl alpha-beta dehydrotrytophanamide", 1988, pp. 1273–1279.
Ito, et al., "Enzymatic modification of tryptophan residues by tryptophan side chain oxidase I and II from Pseudomonas", 1981, pp. 7834–7843.
Takai, et al., "Enzymatic dehydrogenation of tryptophan residues of human globins by tryptophan side chain oxidase II", 1984, pp. 4452–4457.
Davis, et al., "metabolism of N-carbobenzoxyl-L-tryptophan by Chromobacterium violaceum", 1975, pp. 133–144.

*Primary Examiner*—Douglas W. Robinson
*Assistant Examiner*—Jon P. Weber
*Attorney, Agent, or Firm*—Oblon, Spivak, McClelland, Maier & Neustadt

[57] ABSTRACT

Purified enzymatic preparation derived from *Chromobacterium violaceum*, having a dehydrogenase activity, method for preparing it and its use in the production of α,β-dehydrotryptophanyl-peptides.

The said method for preparing α,β-dehydrotryptophanyl-peptides and α,β-dehydrotryptophanyl-proteins is characterised in that one brings into contact:
 a peptide or a protein to be converted, and
 a purified enzymatic preparation having an L-tryptophan dehydrogenase activity and having a specific activity of between 35 and 45 units.seconds$^{-1}$ per mole of heme for N-acetyl-L-tryptophanamide (NATA), an apparent molecular weight of the order of 680 kDa, an isoelectric point of the order of 4, a temperature optimum for activity greater than 80° C. and a temperature stability, at a pH of between 3 and 8 and at a temperature of between 20° and 60° C.

Use of the dehydropeptides and dehydroproteins obtained as probes, reagents, drugs or cosmetic products.

4 Claims, 9 Drawing Sheets

```
┌─────────────────────────────────────────────────────────────┐
│ THAWING-RINSING:                                            │
│ BACTERIA STORED AT −80°C, THAWED IN BUFFER A, 1 ml/g, 4°C   │
│ CENTRIFUGATION 10 MIN., 5,000 g, 4°C                        │
│                                                             │
│ GRINDING:                                                   │
│ BACTERIAL PELLET TAKEN UP IN BUFFER A + 5% GLYCEROL (ABOUT  │
│ 0.4 ml/g) GRINDING IN EATON PRESS AT −60°C                  │
│ THAWING FOLLOWED BY CENTRIFUGATION FOR 20 MIN., 39,000 g, 4°C│
└─────────────────────────────────────────────────────────────┘
            ↙                              ↘
PELLET C1 (ELIMINATED)              SUPERNATANT S1
(CELL DEBRIS, PIGMENT AND THE LIKE) (CRUDE EXTRACT)
                                            ↓
         ┌───────────────────────────────────────────────┐
         │ ULTRACENTRIFUGATION 1 HOUR AT 100,000 g, 4°C  │
         └───────────────────────────────────────────────┘
            ↙                              ↘
PELLET C2 (ELIMINATED)              SUPERNATANT S2
(RIBOSOMES, PIGMENT AND THE LIKE)
                                            ↓
┌─────────────────────────────────────────────────────────────┐
│ DNA-RNA LYSIS                                               │
│ LYSIS BY BENZONASE (MERCK) 25 U/ml, 1 HOUR AT 30°C          │
│ (ADDITION OF g/CMgCl₂, 10 mM)                               │
└─────────────────────────────────────────────────────────────┘
                              ↓
┌─────────────────────────────────────────────────────────────┐
│ FRACTIONAL PRECIPITATION:                                   │
│ PRECIPITATION WITH 20%-SAT. AMMONIUM SULPHATE               │
│ CENTRIFUGATION FOR 20 MIN., 39,000 g, 4°C                   │
└─────────────────────────────────────────────────────────────┘
            ↙                              ↘
PELLET C3 (ELIMINATED)              SUPERNATANT S3
(PROTEINS, NUCLEOTIDES AND THE LIKE)
                                            ↓
┌─────────────────────────────────────────────────────────────┐
│ PRECIPITATION WITH 45%-SAT. AMMONIUM SULPHATE               │
│ CENTRIFUGATION FOR 20 MIN., 39,000 g, 4°C                   │
└─────────────────────────────────────────────────────────────┘
            ↙                              ↘
PELLET C45%                         SUPERNATANT S45%
(BROWN)                             (ELIMINATED)
```

FIG. 7A

SOLUBILISATION OF PELLET C45% IN BUFFER B

↓

FILTRATION:
FILTRATION ON *SEP-PAK ACCELL CM* CARTRIDGE (WATERS)
RINSING IN BUFFER B

↓

ION-EXCHANGE CHROMATOGRAPHY:
ADSORPTION ON *PROTEIN PAK DEAE 8HR* COLUMN (WATERS)
ELUTION IN BUFFER B (0.2 TO 1 M NaCl GRADIENT)

↓

ACTIVE FRACTION Q1 INCUBATED:
3M UREA, 170 mM DTT, 30 MIN. AT 25°C

↓

GEL PERMEATION
SEPARATION ON *ZORBAX GF 450* COLUMN
ELUTION IN BUFFER C

↓

STORAGE:
ACTIVE FRACTIONS Z1 STORED AT −80°C
(20% GLYCEROL)

---

BUFFER A: 0.1 M Tris-HCl, pH 7.0
5 mM EDTA, 100 mg/l PMSF,
1% CHAPS, 10 mM DTT
BUFFER B: 20 mM L-His-HCl, pH 5.6
BUFFER C: 0.2 M $K_2HPO_4$, pH 7

FIG.7B

PURIFIED ENZYMATIC PREPARATION DERIVED FROM *CHROMOBACTERIUM VIOLACEUM*, METHOD FOR PREPARING IT AND ITS USE IN THE PRODUCTION OF α,β-DEHYDROTRYPTOPHANYL-PEPTIDES

BACKGROUND OF THE INVENTION

1. Field of the Invention

The present invention relates to a purified enzymatic preparation derived from *Chromobacterium violaceum*, having a dehydrogenase activity, to a method for preparing it and to its use in the production of α,β-dehydrotryptophanyl peptides.

2. Discussion of the Background

A dehydrogenase activity, which acts on the side chain of tryptophan, has been described in Methods in Enzymology (1987, 142, 195–217; K. TAKAI and O. HAYAISHI). Tryptophan side chain oxidase (TSO), which is isolated from Pseudomonas XA (ATCC 29574), is a multi-enzymatic system which catalyses a dehydrogenation of tryptophanyl residues in the $C_\alpha$ and $C_\beta$ positions. However, the unsaturated compound (—ΔTrp—) is only a by-product of the catabolism of tryptophan which is formed in equilibrium with the degradation products (β-hydroxy and β-keto) from a single indolyloxazoline intermediate and does not enable the production of dehydro compounds to be controlled satisfactorily because of the variation in the yield of synthesis of these compounds, especially as a function of the nature of the substrate and the experimental conditions (the pH in particular). Furthermore, this enzyme has a low specificity and converts L-tryptophan (L-Trp), D-tryptophan (D-Trp), residues whose indole ring is modified or substituted (5 OH-Trp) and decarboxylated residues (tryptamine).

P. J. DAVIS et al. have demonstrated the existence of a biotransformation of N-benzyloxycarbonyl-L-tryptophan in a culture of the Gram-negative bacterium, *Chromobacterium violaceum* (ATCC 12472), which also results in the formation of a double bond between the $C_\alpha$ and $C_\beta$ carbons of L-tryptophan (BBA, 1975, 385, 133–144); they also studied the conversion of indole-3-propionic acid to indole-3-acrylic acid (J. Bacteriol., 1976, 126, 1, 544–546) and the stereochemistry of the dehydrogenation of the side chain of N-benzyloxycarbonyl-(S)-tryptophan (J.C.S. Chem. Comm., 1977, 821, 842–843).

However, this reaction has been demonstrated only on specific substrates whose only common characteristic is the presence of an indole ring, and this only during incubation of resting cells and in bacteria cultures.

It follows from the above that both the reactions described in TAKAI et al. and those described in DAVIS et al. do not permit their use in the production of pure dehydropeptides and dehydroproteins.

SUMMARY OF THE INVENTION

The aim of the present invention is therefore to provide a purified enzymatic preparation having a dehydrogenase activity which is specific for the L-tryptophan residue, from *Chromobacterium violaceum* which is more suitable for the requirements of practical use than preparations of the prior art, especially in that it enables pure dehydropeptides or dehydroproteins to be obtained under operating conditions which are easy to be implemented industrially.

BRIEF DESCRIPTION OF THE DRAWINGS

FIGS. 7a–b are diagrams detailing the purification of L-Trp dehydrogenase activity in *Chromobacterium violaceum*.

DETAILED DESCRIPTION OF THE PREFERRED EMBODIMENTS

Figure 1:
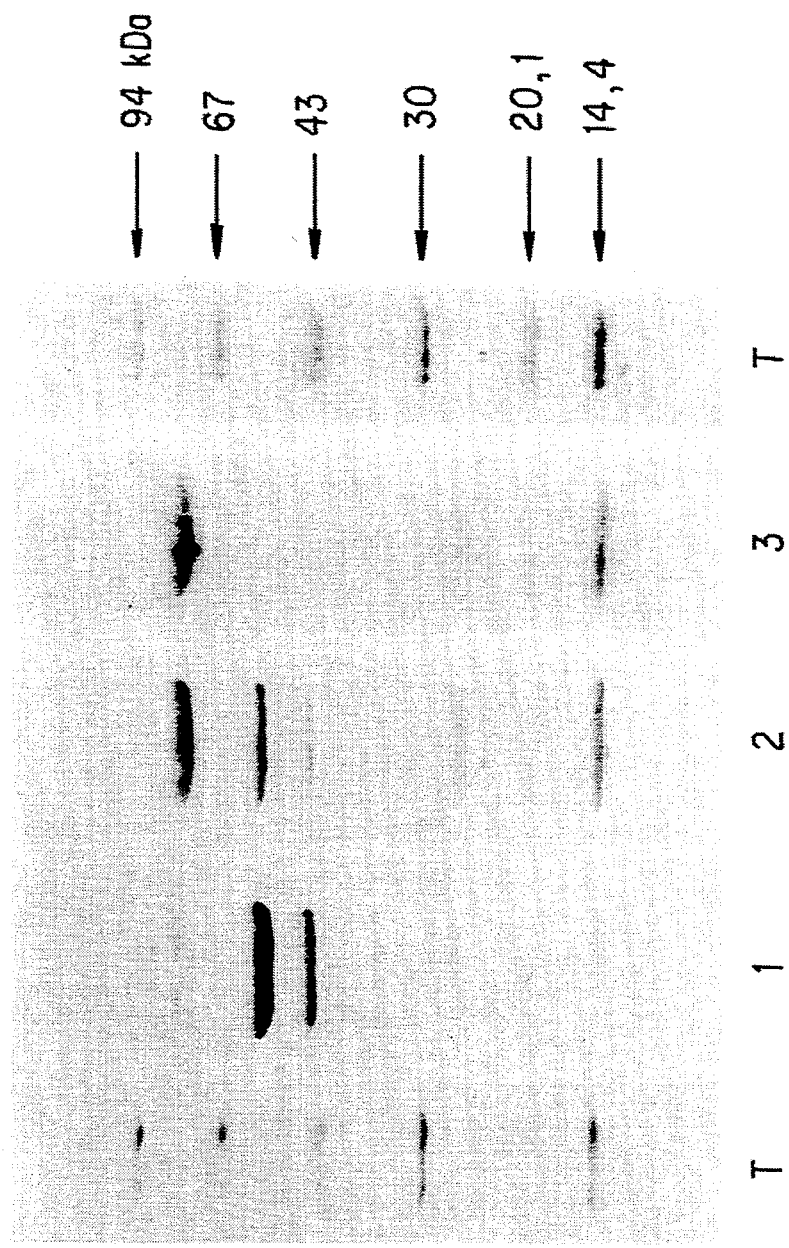
FIG. 1 represents the gel profile of L-Trp 2′,3′-oxidase purified by electrophoresis on a polyacrylamide gel.

The subject of the present invention is a method for preparing α,β-dehydrotryptophanyl-peptides and α,β-dehydrotryptophanyl-proteins, characterised in that one brines into contact:

a peptide or a protein to be converted, and a purified enzymatic preparation having an L-tryptophan dehydrogenase activity and having a specific activity of between 35 and 45 units.seconds$^{-1}$ per mole of heme for N-acetyl-L-tryptophanamide (NATA), an apparent molecular weight of the order of 680 kDa, an isoelectric point of the order of 4, a temperature optimum for activity greater than 80° C. and a temperature stability, at a pH of between 3 and 8 and at a temperature of between 20° and 60° C.

According to an advantageous embodiment of the said method, the conversion is carried out in the presence of catalase (EC 1.11.1.6), at a final concentration of 50 to 100 μg/ml.

According to another advantageous embodiment of the said method, the said purified enzymatic preparation is derived from *Chromobacterium violaceum*.

The inventors have called this purified enzymatic preparation L-tryptophan 2′,3′-oxidase (L-tryptophan: oxygen 2′,3′-oxidoreductase, EC 1.3.3.?), given its functional properties.

Advantageously, and surprisingly, dehydrotryptophan is the only product of the enzymatic reaction catalysed by the L-Trp 2′,3′-oxidase of *Chromobacterium violaceum*, regardless of the reaction conditions between pH 3 and pH 8; furthermore, the dehydro compound obtained is stable when the α-amino group is involved in a peptide bond or is suitably protected.

Also, unexpectedly, under the conditions of the method conforming to the invention, dehydropeptides and dehydroproteins are obtained all of whose accessible tryptophanyl residues have been converted, giving a yield of the order of 100%; furthermore, the dehydro compounds do not necessarily lead to a drastic change in their biological activity.

The creation of a double bond in the $C_\alpha$–$C_\beta$ position of the tryptophanyl residues introduces a conformational stress which confers the following additional properties on the molecule:

inhibition of proteolysis by the major endo and exoproteases: α-chymotrypsin, carboxypeptidase A and carboxypeptidase Y, and aminopeptidase M;

modification of the fluorescence spectrum which enables in particular the interactions involving a specific tryptophanyl residue of the molecule to be specifically studied.

The dehydropeptides and dehydroproteins obtained by the method conforming to the invention are particularly stable and in particular find application:

in the preparation of tracers by virtue of the introduction of stable or radioactive atoms ($^2$D, $^3$H, $^{125}$I and the like) at a specific site of the molecule, such as photoaffinity probes, fluorescence probes or probes for nuclear magnetic resonance (NMR), as reagents for studying the interactions between proteins or for studying the topology of a receptor or of an active site, as diagnostic reagents, including in medical imaging, as new molecules (agonists, antagonists, converting-enzyme inhibitors or any other drug) which are particularly useful especially because of their higher stability (inhibition of proteolytic degradation, enabling prolonged action and better reabsorption of the modified peptide), or as cosmetic products.

The subject of the present invention is also a purified enzymatic preparation having an L-tryptophan dehydrogenase activity which is capable of being used in a method for preparing $\alpha,\beta$-dehydrotryptophanyl-peptides and -proteins conforming to the invention, characterised:

in that it has:
  a specific activity of between 35 and 45 units.-seconds$^{-1}$ per mole of heme for N-acetyl-L-tryptophanamide (NATA),
  an apparent molecular weight of the order of 680 kDa,
  an isoelectric point of the order of 4,
  a temperature optimum for activity greater than 80° C.;
in that it is thermostable; and
in that it catalyses the conversion of tryptophanyl residues to dehydrotryptophanyl residues at a pH of between 3 and 8.

It has a protomeric structure of 88 kDa comprising two subunits of 14 kDa and 74 kDa respectively.

According to an advantageous embodiment of the said preparation, it is capable of being obtained via suitable extraction from *Chromobacterium violaceum*, which extraction comprises an incubation step in a denaturing medium, of the isolated enzymatic fraction.

According to another advantageous embodiment of the said preparation, it is capable of being obtained by expressing, in a suitable microorganism, the genetic information obtained by cloning the gene or cDNA.

The purified enzymatic preparation conforming to the invention has characteristics which enable it to be used industrially:

1. the formation of $\alpha,\beta$-dehydrotryptophanylpeptides and $\alpha,\beta$-dehydrotryptophanyl-proteins results directly from catalysis;
2. these dehydropeptides and these dehydroproteins are the only products of the enzymatic reaction, regardless of the operating conditions between pH 3 and pH 8, provided that the $\alpha$-amino group of the $\Delta$Trp residue is involved in a peptide bond or is suitably protected;
3. the enzyme possesses a high specificity for tryptophanyl residues: (i) with respect to the indole ring which should neither be substituted nor modified, (ii) with respect to the $\alpha$-carbonyl functional group whose presence is essential for the catalysis, and finally (iii) stereospecificity with respect to the asymmetric carbon ($C_\alpha$): the reaction requires the L enantiomer of tryptophan.

The subject of the present invention is also a method for preparing the said purified enzymatic preparation, characterised in that it comprises:

I—a step for preparing the crude enzymatic fraction Q1 which comprises:
  a. the extraction of total proteins by grinding the *Chromobacterium violaceum* cells (available since 1975 from American Type Culture Collection, 12301 Parklawn Drive, Rockville, Md. 20852 under accession number ATCC 12472) in the presence of an inhibitor of the intrinsic proteolytic activity, ultra-centrifugation and separation of the proteins by fractional precipitation in an appropriate buffer, and
  b. the preparation of the enzymatic fraction Q1 by a succession of appropriate chromatographic steps, and II—a step for preparing the purified enzymatic fraction Z1 by:
  c. incubation of the enzymatic fraction Q1 in a denaturing medium, and
  d. gel permeation of the incubated active fraction Q1.

Of the main inhibitors of the endogenous proteolytic activity, there may be mentioned PMSF (phenylmethanesulphonyl fluoride), EDTA (ethylenediaminetetraacetic acid), benzamidine, pepstatin A, leupeptin and the like.

According to an advantageous embodiment of the said method, the inhibitor of the intrinsic proteolytic activity is preferably a mixture of PMSF and EDTA.

In a known manner, the fractional precipitation is carried out using ammonium sulphate or other precipitating agents.

According to yet another advantageous embodiment of the said method, the denaturing medium comprises a denaturing agent chosen from the group comprising urea (3–4M) and SDS (sodium dodecyl sulphate) (0.1 to 2% w/v), combined with a reducing agent chosen from the group comprising dithiothreitol (DTT, >50 mM) and 2-mercaptoethanol (1 to 5% v/v).

Within the context of the present invention, the denaturing medium is defined as a medium which destroys the high- or low-energy interactions within the proteins, with the exception of the enzyme L-Trp 2′,3′-oxidase; the effect of this is a decrease in the apparent molecular weight of the contaminant proteins and a better separation during gel permeation chromatography, the enzymatic activity being stable under these conditions.

In addition to the above arrangements, the invention also comprises other arrangements which will emerge from the following description which refers to exemplary embodiments of the method which is the subject of the present invention.

It should be clearly understood, however, that these examples are given solely as illustration of the subject of the invention and do not constitute in any manner a limitation thereto.

EXAMPLE 1

Preparation of L-Trp 2'3'-oxidase from *Chromobacterium violaceum* (purified enzymatic preparation)

1) Purification:

L-tryptophan dehydrogenase (L-Trp DH) or L-Trp 2',3'-oxidase is prepared from *Chromobacterium violaceum* (ATCC 12472) cells cultured in a Mitoma medium supplemented with 0.5 g/l of L-tryptophan (DAVIS et al., BBA, 1975, 385, 133-144) in a 50-liter fermenter and then stored, after freezing, at −80° C.

The purification, whose procedure is detailed below and in diagram 1, comprises separation of the proteins by grinding, followed by ultracentrifugation and fractional precipitation using ammonium sulphate, preparation of the crude enzymatic fraction Q1 by a succession of chromatographic steps and the preparation of the purified enzymatic fraction Z1 by incubation of the enzymatic fraction Q1 in a denaturing medium and gel permeation of the said fraction.

More specifically:

the *Chromobacterium violaceum* bacteria stored at −80° C. are thawed in a buffer A (0.1M Tris-HCl, pH 7.0, 5 mM EDTA, 100 mg/l PMSF, 1% CHAPS, 10 mM DTT) at a concentration of 1 ml/g and kept at a temperature of 4° C., and then they are centrifuged for 10 minutes at 5,000 g and at 4° C.;

the bacterial pellet is taken up in buffer A, as defined above, supplemented with 5% glycerol (about 0.4 ml/g) and the bacteria-grinding is performed on this pellet in an Eaton press at −60° C.

after performing the grinding, the mixture is again thawed and then centrifuged for 20 minutes at 39,000 g (4° C.);

the supernatant from this centrifugation (supernatant S1) is ultracentrifuged for 1 hour at 100,000 g and at 4° C.;

the supernatant from the ultracentrifugation (supernatant S2) is incubated for 1 hour at 30° C. in the presence of 25 U/ml of Benzonase® (MERCK) and 10 mM MgCl₂ so as to lyse the nuclear material (DNA and RNA);

precipitation with 20%-saturated ammonium sulphate is performed on the lysate obtained and then the fractions are separated by centrifugation at 39,000 g and at 4° C. for 20 minutes;

the supernatant from this final centrifugation (supernatant S3) is precipitated with 45%-saturated ammonium sulphate and centrifuged at 39,000 g and at 4° C. for 20 minutes;

the pellet is recovered (C45%) and is solubilised in a buffer B (20 mM L-His-HCl, pH 5.6), filtered on a Sep-pack ACCELL CM® cartridge (Waters) and rinsed in this buffer B;

the solution obtained is subjected to adsorption chromatography in an anion-exchange column, Protein Pak® DEAE 8HR (Waters) and eluted in buffer B (0.2 to 1M NaCl gradient);

the eluate comprises the active enzymatic fraction Q1 which is incubated with 3M urea and 170 mM DTT for 30 min at 25° C.;

after incubation, the solution is subjected to gel permeation on a ZORBAX GF 450® column (Du Pont de Nemours) followed by elution in buffer C (0.2M K₂HPO₄, pH 7), flow rate 1 ml/min;

the column is equilibrated by means of a standard mixture of proteins of known molecular weight: immunoglobulin M (900,000), thyroglobulin (670,000), γ-globulin (158,000), ovalbumin (44,000), myoglobin (17,000) and cyanocobalamin (1,350); the enzymatic activity is thus eluted in the form of a single protein peak (Z1) whose apparent molecular weight is estimated at 680 kDa and which can be stored at −80° C. (20% glycerol).

2) Purity of the preparation:

electrophoresis in a denaturing medium (SDS-PAGE) shows that the Z1 fraction consists of two major bands: 74 and 14 kDa (FIG. 1).

This FIG. 1 represents the profile of the purification of L-Trp 2',3'-oxidase by electrophoresis on a polyacrylamide gel (8-18% gradient) containing sodium dodecyl sulphate (1 g/l), pH 6.4, and staining with Coomassie blue; the T profiles are molecular weight markers: phosphorylase b (94 kDa), bovine serum albumin (67 kDa), ovalbumin (43 kDa), carbonic anhydrase (30 kDa), trypsin inhibitor (20.1 kDa) and α-lactalbumin (14.4 kDa); well 1 corresponds to fraction C45% ($\approx$50 μg); well 2 corresponds to fraction Q1 ($\approx$50 μg) and well 3 correspond to the pure fraction Z1 (=20 μg).

The spectrum of the enzymatic fraction Z1 reveals the presence of a heme-containing cofactor (FIG. 2). The purity of the preparation may be estimated from the ratio UV/γ of the absorbances at 275 nm (region for aromatics) and at 427 nm (Soret band (γ) for oxidised heme). Indeed, this ratio decreases during the purification and changes from about 3 after ion-exchange chromatography (Q1) to 0.7 after gel permeation (Z1, purity >95%). From this value, the molar extinction coefficient for oxidised heme at 427 nm can be deduced by approximation, that is to say $\epsilon_{427} \approx 120$ mM$^{-1}$.cm$^{-1}$, which enables the enzyme concentration of the preparation to be calculated.

The overall purification yield is about 6.5 mg of L-Trp 2',3'-oxidase per 100 grams of wet cells.

Figure 2A:
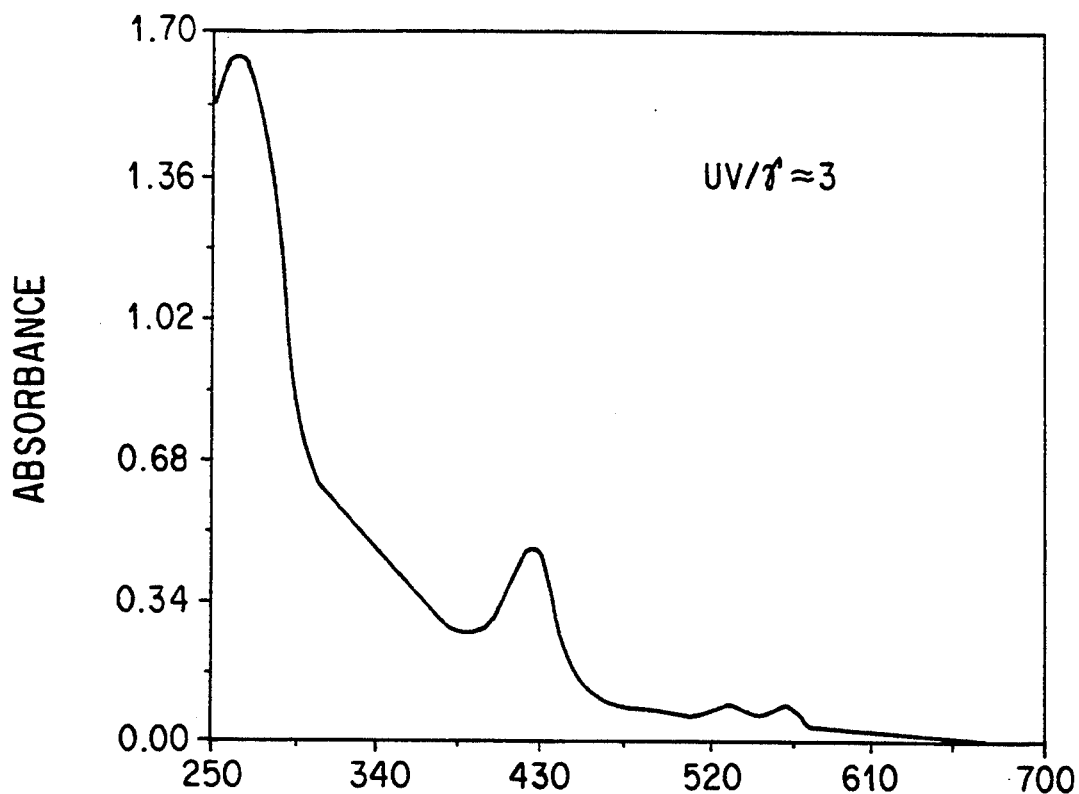
FIGS. 2a–b illustrate the UV spectra of L-Trp 2′,3′-oxidase.
Figure 2B:
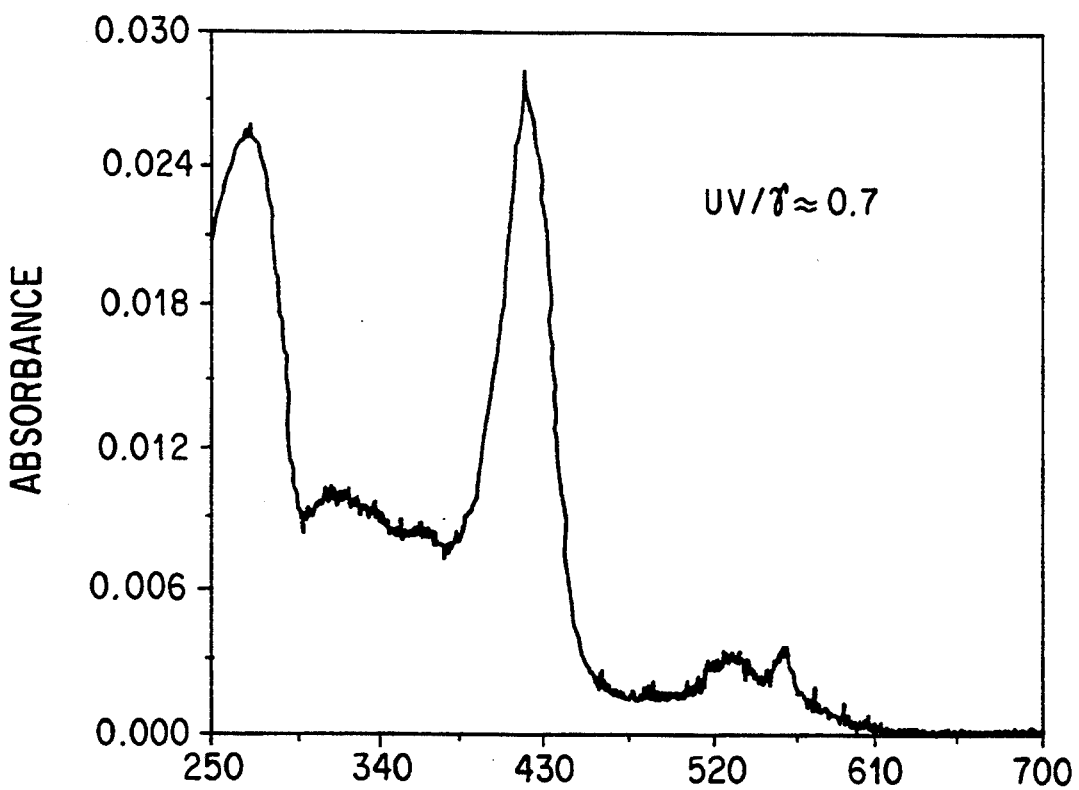

FIGS. 2A and 2B illustrate the spectra for L-Trp 2',3'-oxidase; FIG. 2A corresponds to fraction Q1, the enzyme ($\approx$2.7 μm) being in solution in 20 mM L-histidine—0.2M NaCl buffer, pH 5.6; FIG. 2B corresponds to the pure fraction Z1, the enzyme ($\approx$0.18 μM) being in solution in 0.2M K₂HPO₄ buffer, pH 7. These figures show the wavelength on the x-axis and the absorbance on the y-axis.

3) Storage:

Optimum conditions for stability are obtained in 0.1M Bis-Tris buffer, pH 7. Fractions Q1 and Z1 are preserved frozen at −80° C.

4) Measurement of the enzymatic activity:

Measurements of the specific activity of the enzyme as well as all the kinetic experiments in the steady state, were performed under the standard conditions defined below:

Temperature: 30° C.

Substrate: 1 mM N-acetyl-L-tryptophanamide (NATA)

Figure 3:
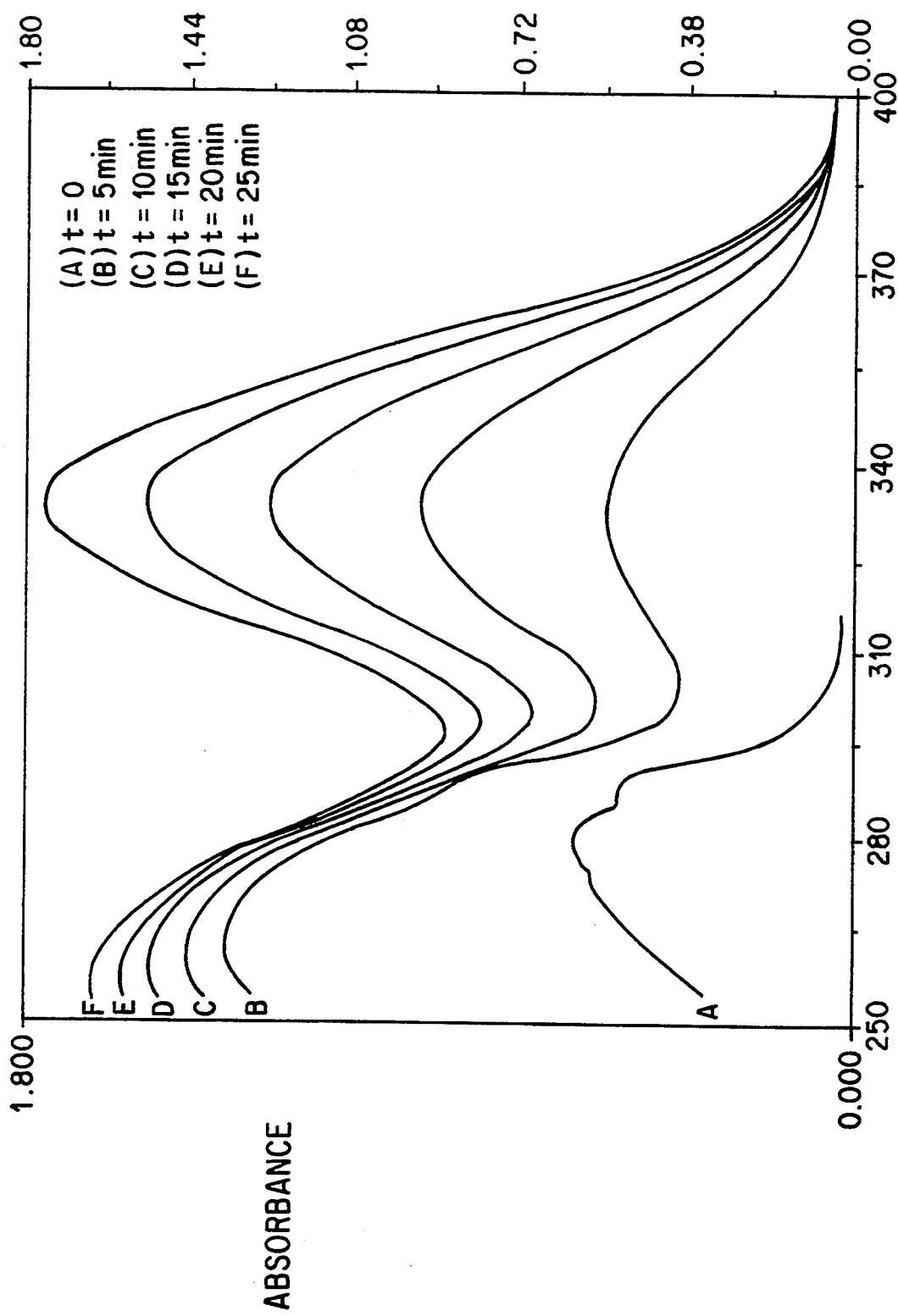
FIG. 3 depicts of the specific activity of purified L-Trp 2′,3′-oxidase measured at 330 nm.

Buffer: 50 mM succinate, pH 5.5 by directly monitoring the appearance of the dehydro product at 330 nm (FIG. 3). The specific activity (As) of fraction Q1 is calculated on the basis of a molar extinction coefficient at 330 nm of 18.8 mM$^{-1}$.cm$^{-1}$ determined in the laboratory (against $\epsilon_{330}$=19.89 mM$^{-1}$.cm$^{-1}$ in the literature; TAKAI et al. mentioned above). NATA, which represents the smallest peptide chain possible, is used as reference substrate for the enzymatic reaction. The specific activity of the preparation (As) is estimated at 39.5±3.1 units for NATA (an enzymatic unit represents a mole of product formed per second per mole of heme).

This FIG. 3, which comprises the wavelengths on the x-axis and the absorbance on the y-axis, illustrates the kinetics of formation of the double bond in position $C_\alpha-C_\beta$ (dehydrogenation of N-acetyl-L-tryptophanamide), under the operating conditions specified above (0.1 mM NATA).

5) Characterisation of the enzyme:

Structure: L-tryptophan 2'3'-oxidase is a hemoprotein whose apparent molecular weight is close to 680 kDa, as specified above. It is acidic overall: its isoelectric point (pI) is about 4. It is a heteropolymer consisting of two subunits in stoichiometric amounts, 74 and 14 kilodaltons, assembled in the form of an 88-kDa protomer. The protomers are probably functional subunits of the enzyme which constitute by themselves a real electron transport chain, and are assembled in "holo-octameric" form.

Function: L-tryptophan 2',3'-oxidase catalyses the conversion of N-acetyl-L-tryptophanamide (NATA) to $\alpha,\beta$-dehydroNATA at the expense of oxygen, with the formation of one equivalent of hydrogen peroxide ($H_2O_2$).

The enzymatic reaction occurs at an optimum pH of 5±0.5, whereas the zone of optimum stability of the enzyme is pH 7±0.5.

Figure 4:
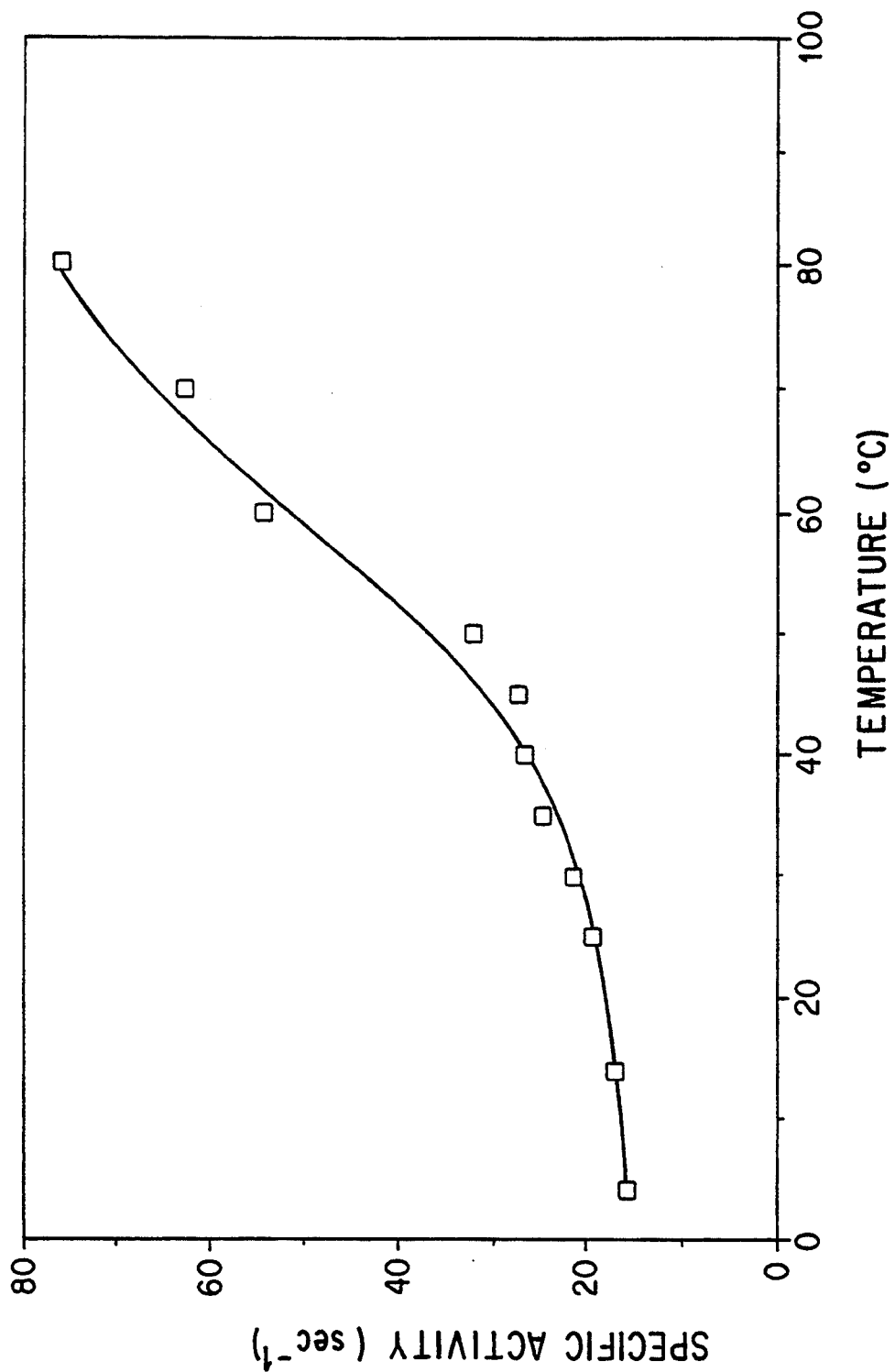
FIG. 4 is a graph illustrating the effect of temperature on the specific activity of L-Trp 2′,3′-oxidase.
Figure 5A:
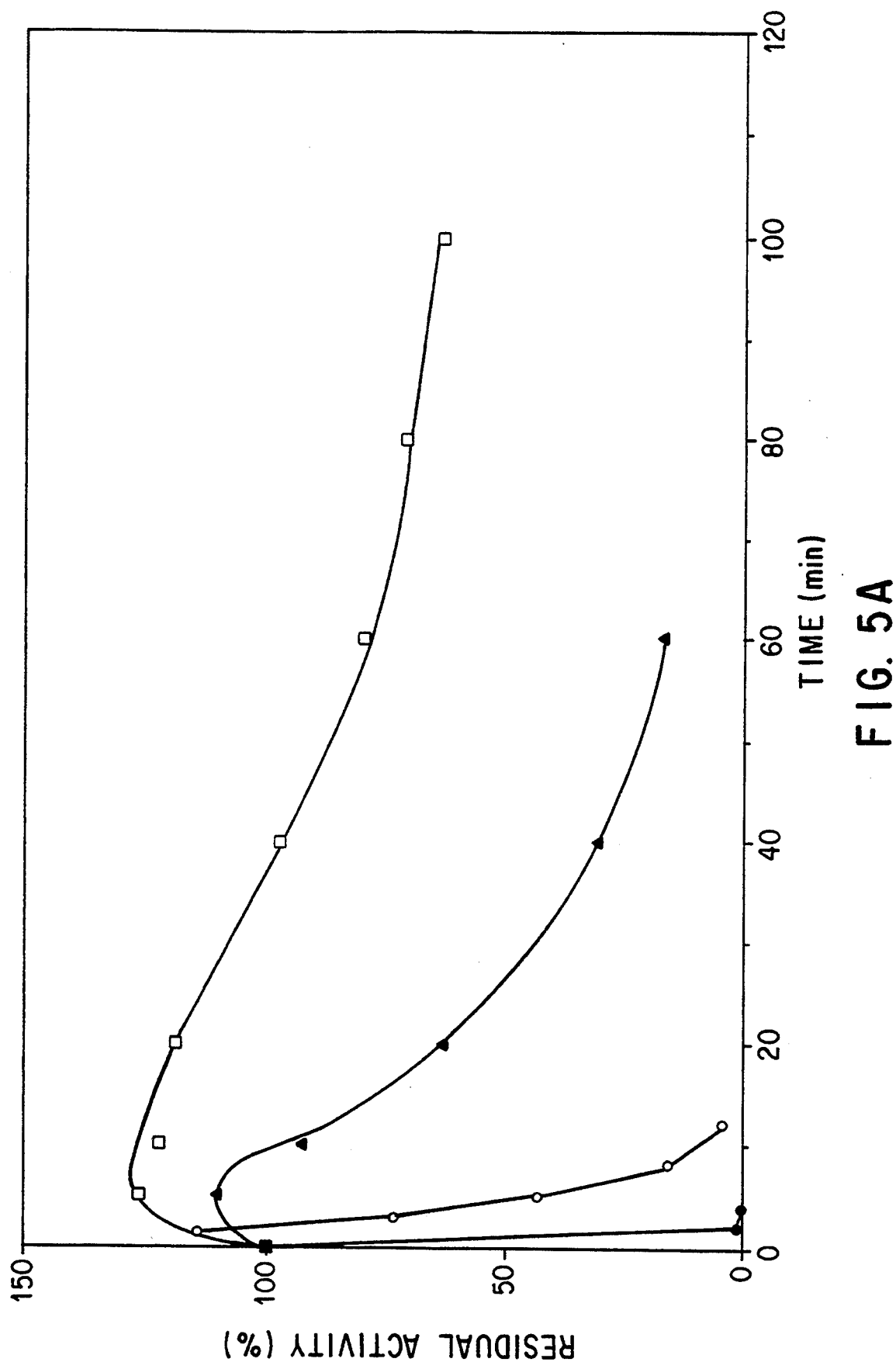
FIG. 5 is a graph illustrating that L-Trp 2′,3′-oxidase is thermally inactivated under first order kinetics.
Figure 5B:
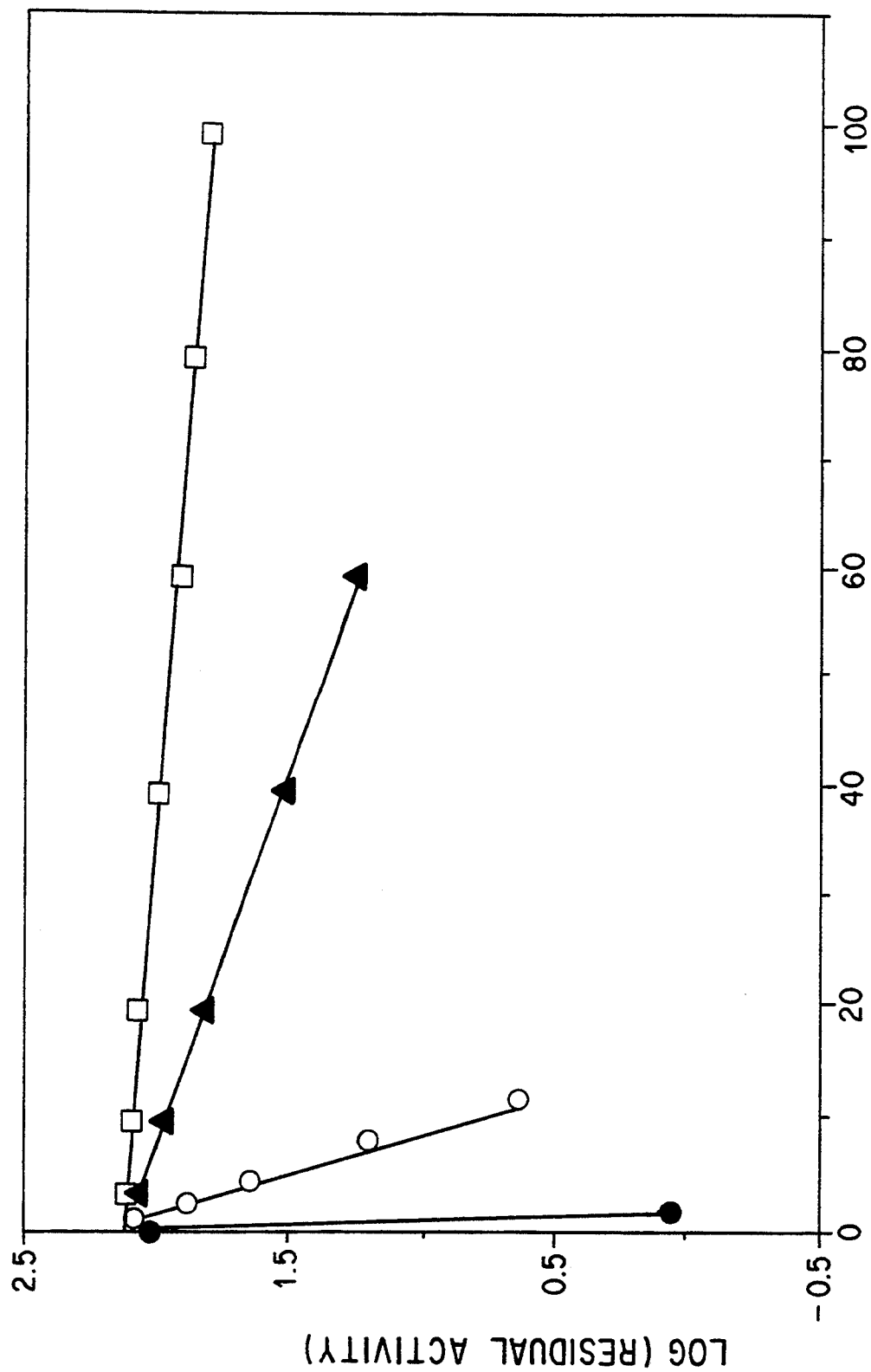

The optimum temperature for the kinetics is above 80° C. (FIG. 4); this FIG. 4, which comprises the temperature on the x-axis and the specific activity on the y-axis, illustrates the effect of temperature on the kinetics; the enzyme is thermostable, which is characterised by a half-life ranging from 90 minutes at 50° C. to only a few seconds above 80° C. FIG. 5 shows that the inactivation follows a first order kinetics, which suggests that thermal denaturation of the enzyme is indeed the only factor involved: the "activated" enzyme (0.27 μM in 0.1M Bis-Tris, pH 7, kept for 3 h at room temperature) is incubated at 50 (□), 60.5 (△), 69 (○) and 80° C. (●); the enzymatic activity is measured as a function of time (standard kinetics test).

6) Specificity of the reaction:

enzyme possesses a high specificity for the indole ring and for the L enantiomer (stereospecificity).

Similarly, no reaction can be observed for tryptamine, whereas indole-3-propionic acid is oxidised to indole-3-acrylic acid; these results demonstrate that the α-amino functional group is not involved in the catalysis whereas the α-carbonyl group is absolutely essential.

7) Characterisation and stability of the reaction products:

The dehydrogenation of NATA was monitored as a function of the pH (pH 3–5, 6–8) at a temperature of 30° C. in 50 mM succinate buffer, pH 5.6. The reaction products are analysed and purified by reversed-phase HPLC and then freeze-dried and analysed by mass spectrometry (desorption by chemical ionisation: DCI). ΔNATA is the only product of the enzymatic reaction which is characterised by HPLC (single peak, γmax 333 nm) and by mass spectrophotometry (MH+ =244).

Figure 6:
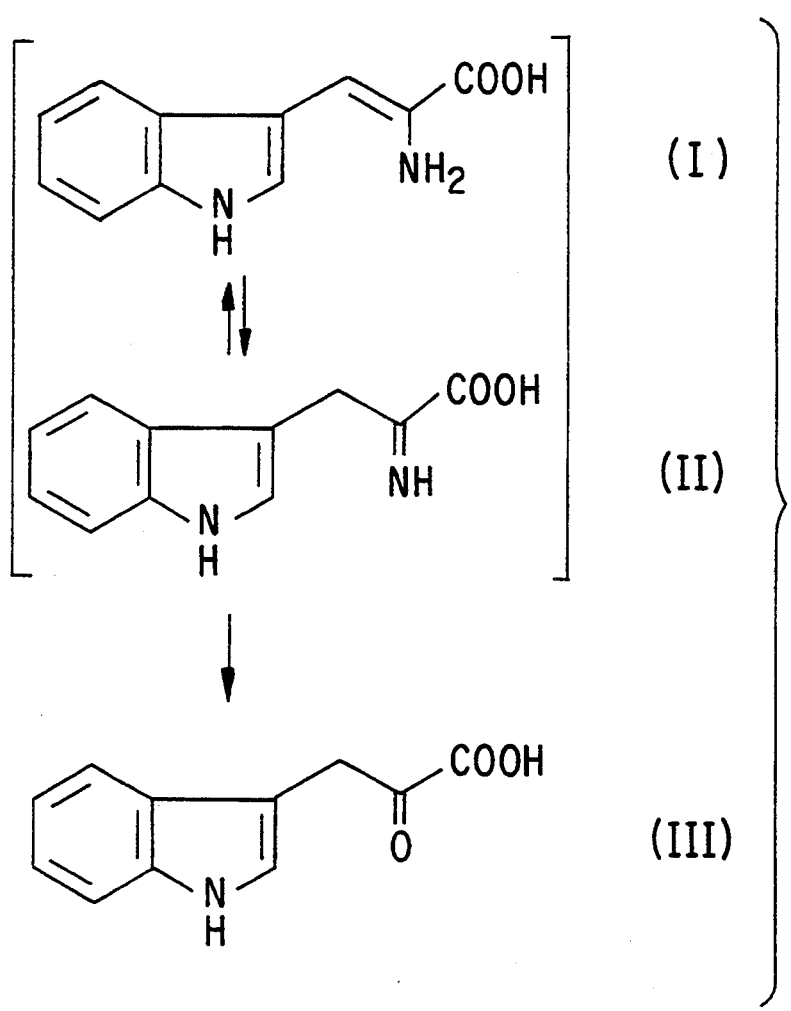
FIG. 6 is a schematic of the conversion of L-Tryptophan to indole-3-pyruvic acid.

The conversion of L-tryptophan and L-tryptophanamide, whose respective α-amino functional groups are free, results in an increase in absorbance at 320 nm followed after a few minutes by a decreasing phase which is accompanied by the complete inhibition of the enzyme. Mass spectrometric analysis of the L-TrpNH$_2$ reaction products reveals a molecular peak (MH+ =203) which probably corresponds to the α-keto derivative: indole-3-pyruvic acid amide. This phenomenon is much more rapid when the α-carboxyl functional group is not substituted (L-Trp, comp. I), and results in the formation of an unstable imine (II) which is hydrolysed to give rise to the α-keto compounds (indole-3-pyruvic acid (III) and its amide homologue respectively)—FIG. 6—. It is therefore preferable to block the α-amino functional group so as to avoid any isomerisation phenomenon and to ensure greater stability of the dehydro compound.

EXAMPLE 2

Method for preparing the Dehydropeptides and Dehydroproteins a) Peptides:

The procedure is as in Example 1.7).

All the reactions were performed in the presence of catalase. In each case, the kinetic constants (Kcat and Km) are calculated so as to evaluate the efficiency of the enzyme for each type of substrate. The results are presented in Table I below.

TABLE I

| SUBSTRATES | Number of residues | SEQUENCE | Km (μM) | Kcat (s$^{-1}$) | Kcat/Km (M$^{-1}$.s$^{-1}$) |
|---|---|---|---|---|---|
| Pentagastrin | 5 | BocβAWMDF | 26 | 32 | 10$^6$ |
| LHRN | 10 | pEHWSYGLRPG | 71 | 20 | 3.10$^5$ |
| KKacoR 15 | 17 | KKKHWVYYTCCPDTPYL | 272 | 2 | 7.10$^3$ |
| ACTH | 24 | SYSMEHFRWGKPVGKKRRPVKVYP | 930 | 17 | 2.10$^4$ |
| β-Lactoglobulin | 162 | Trp$^{19}$-Trp$^{51}$ | | 2% of conversion (*) | |
| Catalase | 506 | Trp$^{14}$-Trp$^{142}$-Trp$^{182}$-Trp$^{185}$-Trp$^{276}$-Trp$^{302}$ | | 12% of conversion (*) | |
| BSA | 582 | Trp$^{133}$-Trp$^{212}$ | | 24% of conversion (*) | |

(*): Values given as a guide, giving an idea of the conversion of Trp in the proteins in 24 hours, under the standard conditions defined in Example 1.7 for NATA (E/S ≃ 1/1000).

No conversion could be observed for the aromatic amino acids: N-acetyl-L-phenylalaninamide and N-acetyl-L-tyrosinamide. The same is the case when the indole ring is substituted: 5-hydroxyl L-Trp, N-formyl L-Trp and for the isomers of the D series: D-tryptophan and N-acetyl-D-tryptophan. These results show that the Generally, the efficiency of the enzyme decreases as a function of the peptide size. However, the Kcat remains at the same order of magnitude except in the case of the KKacoR15 peptide (synthetic peptide of the α subunit of the acetylcholine nicotinic receptor) where it is decreased by a factor of 10; this result can be explained by the very hydrophobic and compact nature of this peptide and by the presence of a disulphide bridge. The Km undergoes a larger variation which can reach a factor of 50 for a peptide of 24 amino acids. In all cases, regardless of the position of the tryptophanyl residue in the sequence, the peptides tested, up to 25 residues, were successfully converted ($\lambda$max 332 to 336 nm). The yields are practically up to 100%.

b) Proteins:

As specified above, the accessibility of the tryptophanyl residues, both with respect to the indolyl ring and with respect to the $C_\alpha$ and $C_\beta$ protons, plays a major role. The conversion is very slow; however, the yields obtained, in 24 hours, under standard conditions, using large proteins ($\beta$-lactoglobulin: 32 kDa, BSA: 67 kDa, catalase: 232 kDa) show that, under suitable conditions (temperature, pH, partial denaturing medium and the like), the conversion of the accessible tryptophanyl residues may be up to 100%.

c) Specific properties of the dehydropeptides:

The creation of a double bond in the $C_\alpha$-$C_\beta$ position of the tryptophanyl residues introduces a conformational stress which confers new properties on the molecule:

Resistance to proteolysis:

The presence of $\alpha,\beta$-dehydrotryptophanyl residues within the polypeptide chains completely inhibits proteolysis by the major endo- and exoproteases: $\alpha$-chymotrypsin, carboxypeptidase A and carboxypeptidase Y, and aminopeptidase M. The dehydro compounds therefore constitute a resistant link inside the molecule and may make it possible to prolong the action and to enhance the reabsorption of a peptide drug.

Modification of the fluorescence spectrum:

The fluorescence spectra of NATA and ANATA as well as the major synthetic dehydro-peptides were recorded. The presence of the double bond causes a displacement of the wavelength of maximum emission which changes from 372 nm ($\lambda$exc.: 280 nm) to 427 nm ($\lambda$exc.: 330 nm). This modification of the emission spectrum is therefore particularly important since it enables the interactions affecting a specific tryptophanyl residue of the molecule to be specifically studied.

Biological activity:

The conformational stresses induced in a peptide—or a protein—by the formation of $\alpha,\beta$-dehydrotryptophan may result in localised structural modifications which are capable of causing the destruction or, on the contrary, the intensification of its biological activity.

[$\Delta$Trp$^3$]pentagastrin was tested in vivo and the results show that this peptide has the same biological activity as the native peptide.

It follows therefrom that the formation of dehydrotryptophan does not necessarily cause a drastic change in the biological activity of the tested products.

Use of the double bond for the introduction of specific probes:

The dehydrotryptophanyl residues generated in situ within the peptides and proteins constitute an advantageous site for labelling.

The reduction of the double bond with tritium gas ($^3$H$_2$), in the presence of a stereospecific catalyst, has already been performed using the reference $\Delta$NATA (PINTOALPHANDARY H. et al., J. Label. Comp. & Radiopharmaceuticals, 1988, 25, 1273–1279). This method has numerous advantages because of its specificity, the high similarity of the tritium atom to the hydrogen atom—absence of modification of the primary structure—, the high specific radioactivity of this isotope (29 Ci/mat) and its long half-life (12.6 years). The addition of non-radioactive or radioactive iodine (ICl, pH 7) to the double bond is a second possibility (MAELICKE et al., FEBS Lett., 1978, 85, 296–300).

As evident from the above, the invention is not in the least limited to the implementations, embodiments and applications which have just been described more explicitly, on the contrary, it embraces all the variants which may come to the mind of a specialist in this field, without departing from the framework or the scope of the present invention.

We claim:

1. A method for preparing $\alpha,\beta$-dehydrotryptophanyl-peptides and $\alpha,\beta$-dehydrotryptophanyl-proteins, comprising treating a solution of a peptide or a protein containing accessible tryptophans at a pH of from 3 to 8 and at a temperature of between 20° and 60° C. with a purified enzymatic preparation obtained from *Chromobacterium violaceum* having:
(i) L-tryptophan dehydrogenase activity,
(ii) a specific activity of between 35 and 45 units for N-acetyl-L-tryptophanamide (NATA), wherein said units represents a mole of product formed per second per mole of heme,
(iii) an apparent molecular weight of approximately 680 kDa,
(iv) an isoelectric point of about 4, and
(v) a temperature optimum for activity greater than 80° C.

2. The method according to claim 1, wherein said conversion is carried out in the presence of catalase (EC 1.11.1.6), at a final concentration of 50 to 100 $\mu$g/ml.

3. A purified enzymatic preparation derived from *Chromobacterium violaceum* having:
(i) L-tryptophan dehydrogenase activity,
(ii) a specific activity of between 35 and 45 units for N-acetyl-L-tryptophanamide (NATA), wherein said units represents a mole of product formed per second per mole of heme,
(iii) an apparent molecular weight of approximately 680 kDa,
(iv) an isoelectric point of about 4, and
(v) a temperature optimum for activity greater than 80° C.;
wherein said preparation catalyzes the conversion of tryptophanyl residues to dehydrotryptophanyl residues at a pH of from 3 to 8.

4. A purified enzymatic preparation obtained from *Chromobacterium violaceum* by:
(i) preparing a crude enzymatic fraction by:
(a) extracting total proteins from *Chromobacterium violaceum* cells by
(i) grinding said cells in the presence of an inhibitor of intrinsic proteolytic activity,
(ii) ultracentrifugating, and
(iii) separating proteins by fractional precipitation in a buffer, and
(b) subsequently fractionating said proteins to obtain an enzymatic fraction Q1 by a succession of chromatographic steps, and
(ii) subsequently purifiying said enzymatic fraction Q1 by
(c) incubating said enzymatic fraction in a denaturing medium comprising (i) 0.1 to 2% w/v of a denaturing agent selected from the group consisting of 3–4M urea and sodium dodecyl sulphate and (ii) 1 to 5% v/v of a reducing agent selected from the group consisting of >50 mM dithiothreitol and 2-mercaptoethanol, and
(d) separating, by gel permeation, said incubated active fraction.

* * * * *